(12) United States Patent
Avni (10) Patent No.: US 7,998,065 B2
(45) Date of Patent: Aug. 16, 2011

(54) IN VIVO SENSING DEVICE WITH A CIRCUIT BOARD HAVING RIGID SECTIONS AND FLEXIBLE SECTIONS

(75) Inventor: Dov Avni, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 49 days.

(21) Appl. No.: 10/481,126

(22) PCT Filed: Jun. 18, 2002

(86) PCT No.: PCT/IL02/00480
§ 371 (c)(1),
(2), (4) Date: Dec. 18, 2003

(87) PCT Pub. No.: WO02/102224
PCT Pub. Date: Dec. 27, 2002

(65) Prior Publication Data
US 2004/0171914 A1    Sep. 2, 2004

Related U.S. Application Data

(60) Provisional application No. 60/298,387, filed on Jun. 18, 2001.

(51) Int. Cl.
*A61B 1/04* (2006.01)
*A61B 1/06* (2006.01)

(52) U.S. Cl. ........ 600/130; 600/109; 600/160; 600/179; 348/76

(58) Field of Classification Search .................. 600/109, 600/110, 129, 130; 348/76; 174/75 F, 255, 174/254; 429/100, 163, 159
See application file for complete search history.

(56) References Cited

U.S. PATENT DOCUMENTS

| 78,134 A | 5/1868 | Robbins |
| 3,322,374 A | 5/1967 | King et al. |
| 3,509,270 A * | 4/1970 | Yorgensen et al. ........... 174/266 |
| 3,529,200 A | 9/1970 | Potter |
| 3,616,532 A * | 11/1971 | Beck ............................... 29/615 |
| 3,683,389 A | 8/1972 | Hollis |
| 3,683,890 A | 8/1972 | Beal |
| 3,771,516 A | 11/1973 | Corriero |
| 3,791,377 A | 2/1974 | Norby et al. |

(Continued)

FOREIGN PATENT DOCUMENTS
DE    2 929 429    2/1980

(Continued)

OTHER PUBLICATIONS

"The Radio Pill", Rowlands, et al., British Communications and Electronics, Aug. 1960, pp. 598-601.

(Continued)

*Primary Examiner* — John P Leubecker
(74) *Attorney, Agent, or Firm* — Pearl Cohen Zedek Latzer, LLP (57) ABSTRACT

A device including at least one image sensor and a circuit board having a plurality of rigid sections and a plurality of flexible sections. The image sensor is disposed an a rigid section of the circuit board. The circuit board may be folded into a housing configured for in vivo sensing. An illumination source is electrically connected to a ring shaped rigid section and at least one battery is positioned between two of the rigid sections.

24 Claims, 3 Drawing Sheets

U.S. PATENT DOCUMENTS

| | | | |
|---|---|---|---|
| 3,856,000 A | 12/1974 | Chikama | |
| 3,971,362 A | 7/1976 | Pope et al. | |
| 4,037,047 A | 7/1977 | Taylor | |
| 4,087,960 A * | 5/1978 | Koichi | 368/205 |
| 4,178,735 A | 12/1979 | Jackson | |
| 4,198,960 A | 4/1980 | Utsugi | |
| 4,239,040 A | 12/1980 | Hosoya et al. | |
| 4,246,792 A | 1/1981 | Matzuk | |
| 4,262,632 A | 4/1981 | Hanton et al. | |
| 4,278,077 A | 7/1981 | Mizumoto | |
| 4,319,563 A | 3/1982 | Kubota | |
| 4,431,005 A | 2/1984 | McCormick | |
| 4,439,197 A | 3/1984 | Honda et al. | |
| 4,447,677 A * | 5/1984 | Miyahra et al. | 381/324 |
| 4,628,150 A * | 12/1986 | Luc | 174/88 C |
| 4,646,724 A | 3/1987 | Sato et al. | |
| 4,668,884 A | 5/1987 | Amao et al. | |
| 4,687,695 A | 8/1987 | Hamby | |
| 4,689,621 A | 8/1987 | Kleinberg | |
| 4,741,327 A * | 5/1988 | Yabe | 600/130 |
| 4,742,183 A * | 5/1988 | Soloway et al. | 174/254 |
| 4,742,817 A | 5/1988 | Kawashima et al. | |
| 4,803,992 A | 2/1989 | Lemelson | |
| 4,807,598 A | 2/1989 | Hasegawa | |
| 4,812,135 A | 3/1989 | Smith | |
| 4,812,726 A | 3/1989 | Benii et al. | |
| 4,819,620 A | 4/1989 | Okutsu | |
| 4,844,076 A * | 7/1989 | Lesho et al. | 600/302 |
| 4,860,732 A | 8/1989 | Hasegawa et al. | |
| 4,936,823 A | 6/1990 | Colvin et al. | |
| 4,939,792 A * | 7/1990 | Urbish et al. | 455/347 |
| 4,940,997 A | 7/1990 | Hamlin et al. | |
| 5,010,412 A | 4/1991 | Garriss | |
| 5,021,888 A | 6/1991 | Kondou et al. | |
| 5,025,704 A * | 6/1991 | Davis | 84/723 |
| 5,042,486 A | 8/1991 | Pfeiler et al. | |
| 5,078,134 A | 1/1992 | Heilman et al. | |
| 5,081,041 A | 1/1992 | Yafuso et al. | |
| 5,109,870 A | 5/1992 | Silny et al. | |
| 5,187,572 A | 2/1993 | Nakamura et al. | |
| 5,206,463 A | 4/1993 | DeMaso et al. | |
| 5,211,165 A | 5/1993 | Dumoulin et al. | |
| 5,217,449 A | 6/1993 | Yuda et al. | |
| 5,219,292 A | 6/1993 | Dickirson et al. | |
| 5,220,198 A | 6/1993 | Tsuji | |
| 5,241,170 A | 8/1993 | Field, Jr. et al. | |
| 5,250,371 A * | 10/1993 | Kleinert et al. | 429/99 |
| 5,267,033 A | 11/1993 | Hoshino | |
| 5,279,607 A | 1/1994 | Schentag et al. | |
| 5,318,024 A | 6/1994 | Kittrell et al. | |
| 5,330,427 A | 7/1994 | Weissenburger | |
| 5,368,027 A | 11/1994 | Lubbers et al. | |
| 5,381,784 A | 1/1995 | Adair | |
| 5,395,366 A | 3/1995 | D'Andrea et al. | |
| 5,398,670 A | 3/1995 | Ortiz et al. | |
| 5,398,689 A * | 3/1995 | Connor et al. | 600/459 |
| 5,420,631 A | 5/1995 | Hamasaki | |
| 5,426,263 A * | 6/1995 | Potter et al. | 174/52.4 |
| 5,429,132 A | 7/1995 | Guy et al. | |
| 5,434,362 A | 7/1995 | Klosowiak et al. | |
| 5,448,511 A * | 9/1995 | Paurus et al. | 365/52 |
| 5,454,366 A * | 10/1995 | Ito et al. | 600/109 |
| 5,472,804 A * | 12/1995 | Austin et al. | 429/99 |
| 5,495,114 A | 2/1996 | Adair | |
| 5,497,935 A | 3/1996 | Essen-Moller | |
| 5,508,781 A | 4/1996 | Imai et al. | |
| 5,549,109 A | 8/1996 | Samson et al. | |
| 5,558,640 A | 9/1996 | Pfeiler et al. | |
| 5,604,531 A | 2/1997 | Iddan et al. | |
| 5,643,175 A | 7/1997 | Adair | |
| 5,679,216 A * | 10/1997 | Takayama et al. | 438/598 |
| 5,681,260 A | 10/1997 | Ueda et al. | |
| 5,697,377 A | 12/1997 | Wittkampf | |
| 5,697,384 A | 12/1997 | Miyawaki et al. | |
| 5,699,121 A | 12/1997 | Zakhor et al. | |
| 5,725,474 A | 3/1998 | Yasui et al. | |
| 5,734,418 A | 3/1998 | Danna | |
| 5,742,804 A | 4/1998 | Yeh et al. | |
| 5,747,996 A | 5/1998 | Fuchs | |
| 5,754,313 A | 5/1998 | Pelchy et al. | |
| 5,754,409 A | 5/1998 | Smith | |
| 5,800,350 A | 9/1998 | Coppleson et al. | |
| 5,807,266 A | 9/1998 | Itonaga et al. | |
| 5,809,161 A | 9/1998 | Auty et al. | |
| 5,812,187 A | 9/1998 | Watanabe | |
| 5,817,015 A | 10/1998 | Adair | |
| 5,819,736 A | 10/1998 | Avny et al. | |
| 5,833,603 A | 11/1998 | Kovacs et al. | |
| 5,837,196 A | 11/1998 | Pinkel et al. | |
| 5,857,963 A | 1/1999 | Pelchy et al. | |
| 5,908,294 A | 6/1999 | Schick et al. | |
| 5,913,820 A | 6/1999 | Bladen et al. | |
| 5,929,901 A | 7/1999 | Adair et al. | |
| 5,940,126 A | 8/1999 | Kimura | |
| 5,984,875 A * | 11/1999 | Brune | 600/549 |
| 5,986,693 A | 11/1999 | Adair et al. | |
| 5,993,378 A | 11/1999 | Lemelson | |
| 5,999,091 A | 12/1999 | Wortham | |
| 6,021,048 A | 2/2000 | Smith | |
| 6,043,839 A | 3/2000 | Adair et al. | |
| 6,058,114 A | 5/2000 | Sethuram et al. | |
| 6,088,606 A | 7/2000 | Ignotz et al. | |
| 6,099,482 A | 8/2000 | Brune et al. | |
| 6,121,922 A * | 9/2000 | Mohan | 342/357.1 |
| 6,142,390 A | 11/2000 | Ito et al. | |
| 6,149,581 A | 11/2000 | Klingenstein | |
| 6,174,291 B1 | 1/2001 | McMahon et al. | |
| 6,188,355 B1 | 2/2001 | Gilboa | |
| 6,208,698 B1 | 3/2001 | Marchesani et al. | |
| 6,228,048 B1 | 5/2001 | Robbins | |
| 6,233,476 B1 | 5/2001 | Strommer et al. | |
| 6,240,312 B1 | 5/2001 | Alfano et al. | |
| 6,273,904 B1 | 8/2001 | Chen et al. | |
| 6,276,605 B1 | 8/2001 | Olmstead et al. | |
| 6,285,897 B1 | 9/2001 | Kilcoyne et al. | |
| 6,300,946 B1 | 10/2001 | Lincke et al. | |
| 6,304,769 B1 | 10/2001 | Arenson et al. | |
| 6,313,456 B1 * | 11/2001 | Miyashita et al. | 250/208.1 |
| 6,324,418 B1 * | 11/2001 | Crowley et al. | 600/476 |
| 6,338,347 B1 * | 1/2002 | Chung | 600/9 |
| 6,366,186 B1 | 4/2002 | Hill et al. | |
| 6,369,812 B1 | 4/2002 | Iyriboz et al. | |
| 6,371,927 B1 * | 4/2002 | Brune et al. | 600/549 |
| 6,395,562 B1 | 5/2002 | Hammock et al. | |
| 6,396,438 B1 | 5/2002 | Seal | |
| 6,400,338 B1 | 6/2002 | Mejia et al. | |
| 6,415,181 B1 | 7/2002 | Schu et al. | |
| 6,417,885 B1 * | 7/2002 | Suzuki et al. | 348/374 |
| 6,428,469 B1 | 8/2002 | Iddan et al. | |
| 6,449,006 B1 * | 9/2002 | Shipp | 348/70 |
| 6,454,437 B1 * | 9/2002 | Kelly | 362/246 |
| 6,475,145 B1 | 11/2002 | Baylor | |
| 6,488,694 B1 | 12/2002 | Lau et al. | |
| 6,547,721 B1 | 4/2003 | Higuma et al. | |
| 6,547,723 B1 | 4/2003 | Ouchi | |
| 6,584,348 B2 | 6/2003 | Glukhovsky | |
| 6,603,103 B1 | 8/2003 | Ulrich et al. | |
| 6,607,301 B1 | 8/2003 | Glukhovsky et al. | |
| 6,632,175 B1 | 10/2003 | Marshall | |
| 6,692,430 B2 | 2/2004 | Adler | |
| 6,709,387 B1 | 3/2004 | Glukhovsky et al. | |
| 6,711,423 B2 | 3/2004 | Colvin, Jr. | |
| 6,764,440 B2 | 7/2004 | Iddan et al. | |
| 6,796,939 B1 * | 9/2004 | Hirata et al. | 600/179 |
| 6,800,060 B2 | 10/2004 | Marshall | |
| 6,836,377 B1 | 12/2004 | Kislev et al. | |
| 6,887,196 B2 | 5/2005 | Arai et al. | |
| 6,934,573 B1 | 8/2005 | Glukhovsky et al. | |
| 6,939,290 B2 | 9/2005 | Iddan | |
| 6,939,292 B2 | 9/2005 | Mizuno | |
| 6,944,031 B2 | 9/2005 | Takami | |
| 6,944,316 B2 | 9/2005 | Glukhovsky et al. | |
| 6,950,690 B1 | 9/2005 | Meron et al. | |
| 6,951,536 B2 | 10/2005 | Yokoi et al. | |
| 6,958,034 B2 | 10/2005 | Iddan | |
| 6,958,035 B2 | 10/2005 | Friedman et al. | |
| 7,009,634 B2 | 3/2006 | Iddan et al. | |

| | | |
|---|---|---|
| 7,022,067 B2 | 4/2006 | Glukhovsky et al. |
| 7,039,453 B2 | 5/2006 | Mullick et al. |
| 7,044,908 B1 | 5/2006 | Montalbo et al. |
| 7,104,952 B2 | 9/2006 | Iddan et al. |
| 7,118,529 B2 | 10/2006 | Glukhovsky et al. |
| 7,833,151 B2 | 11/2010 | Khait et al. |
| 2001/0006252 A1* | 7/2001 | Kim et al. .................. 257/688 |
| 2001/0017649 A1 | 8/2001 | Yaron |
| 2001/0025135 A1 | 9/2001 | Naito et al. |
| 2001/0035902 A1 | 11/2001 | Iddan et al. |
| 2001/0051766 A1* | 12/2001 | Gazdzinski .................. 600/309 |
| 2002/0015952 A1 | 2/2002 | Anderson et al. |
| 2002/0032366 A1 | 3/2002 | Iddan |
| 2002/0095187 A1 | 7/2002 | Thompson et al. |
| 2002/0102224 A1 | 8/2002 | Lim |
| 2002/0103417 A1 | 8/2002 | Gazdzinski |
| 2002/0109774 A1 | 8/2002 | Meron |
| 2002/0143239 A1 | 10/2002 | Henzler et al. |
| 2002/0146368 A1 | 10/2002 | Meron et al. |
| 2002/0158975 A1 | 10/2002 | Hiroshige et al. |
| 2002/0158976 A1 | 10/2002 | Vni et al. |
| 2002/0165592 A1 | 11/2002 | Glukhovsky |
| 2002/0171669 A1 | 11/2002 | Meron et al. |
| 2002/0173718 A1 | 11/2002 | Frisch et al. |
| 2002/0177779 A1 | 11/2002 | Adler et al. |
| 2002/0193664 A1 | 12/2002 | Ross et al. |
| 2002/0198439 A1 | 12/2002 | Mizuno |
| 2003/0011472 A1 | 1/2003 | Lewkowicz |
| 2003/0013370 A1 | 1/2003 | Glukhovsky |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0032863 A1 | 2/2003 | Kazakevich |
| 2003/0040685 A1 | 2/2003 | Lewkowicz |
| 2003/0043263 A1 | 3/2003 | Glukhovsky et al. |
| 2003/0045790 A1 | 3/2003 | Lewkowicz et al. |
| 2003/0060734 A1 | 3/2003 | Yokoi |
| 2003/0073935 A1 | 4/2003 | Segawa et al. |
| 2003/0077223 A1 | 4/2003 | Glukhovsky |
| 2003/0085994 A1 | 5/2003 | Fujita |
| 2003/0114742 A1 | 6/2003 | Lewkowicz et al. |
| 2003/0117491 A1 | 6/2003 | Avni et al. |
| 2003/0130562 A1 | 7/2003 | Barbato et al. |
| 2003/0151661 A1 | 8/2003 | Davidson |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0195400 A1 | 10/2003 | Glukhovsky |
| 2003/0195415 A1 | 10/2003 | Iddan |
| 2003/0208107 A1 | 11/2003 | Rafel |
| 2003/0214579 A1 | 11/2003 | Iddan |
| 2003/0214580 A1 | 11/2003 | Iddan |
| 2003/0216622 A1 | 11/2003 | Meron et al. |
| 2003/0227547 A1 | 12/2003 | Iddan |
| 2004/0027459 A1 | 2/2004 | Segawa et al. |
| 2004/0027500 A1 | 2/2004 | Davidson et al. |
| 2004/0059568 A1 | 3/2004 | Talkin |
| 2004/0073087 A1 | 4/2004 | Glukhovsky |
| 2004/0087832 A1 | 5/2004 | Glukhovsky et al. |
| 2004/0106849 A1 | 6/2004 | Cho et al. |
| 2004/0109488 A1 | 6/2004 | Glukhovsky |
| 2004/0171914 A1 | 9/2004 | Avni |
| 2004/0215059 A1 | 10/2004 | Homan et al. |
| 2004/0225189 A1 | 11/2004 | Kimoto et al. |
| 2004/0225190 A1 | 11/2004 | Kimoto et al. |
| 2004/0236182 A1 | 11/2004 | Iddan |
| 2004/0254455 A1 | 12/2004 | Iddan |
| 2004/0258328 A1 | 12/2004 | Adler |
| 2005/0025368 A1 | 2/2005 | Glukhovsky |
| 2005/0043583 A1 | 2/2005 | Killmann et al. |
| 2005/0043586 A1 | 2/2005 | Suzushima |
| 2005/0043587 A1 | 2/2005 | Fujimori |
| 2005/0049461 A1 | 3/2005 | Honda et al. |
| 2005/0068416 A1 | 3/2005 | Glukhovsky et al. |
| 2005/0075559 A1 | 4/2005 | Houzego et al. |
| 2005/0124858 A1 | 6/2005 | Matsuzawa |
| 2005/0259487 A1 | 11/2005 | Glukhovsky et al. |
| 2005/0270169 A1 | 12/2005 | Drader et al. |
| 2006/0004256 A1 | 1/2006 | Gilad et al. |
| 2006/0004257 A1 | 1/2006 | Gilad et al. |
| 2006/0015013 A1 | 1/2006 | Gilad et al. |
| 2006/0069310 A1 | 3/2006 | Couvillon |
| 2006/0100496 A1 | 5/2006 | Avron |
| 2006/0104057 A1 | 5/2006 | Avron et al. |
| 2006/0155174 A1 | 7/2006 | Glukhovsky et al. |
| 2006/0241407 A1 | 10/2006 | Scarantino et al. |
| 2006/0241422 A1 | 10/2006 | Muratayev et al. |
| 2006/0264709 A1 | 11/2006 | Fujimori |
| 2007/0118012 A1 | 5/2007 | Gilad et al. |
| 2007/0229656 A1 | 10/2007 | Khait et al. |
| 2008/0021281 A1 | 1/2008 | Fujimori |

FOREIGN PATENT DOCUMENTS

| | | |
|---|---|---|
| DE | 3 440 177 | 5/1986 |
| DE | 34 40 177 | 5/1986 |
| EP | 1 104 182 | 5/2001 |
| EP | 1104182 | 5/2001 |
| FR | 2362566 * | 8/1976 |
| FR | 2362556 | 3/1978 |
| FR | 2 688 997 | 3/1992 |
| GB | 2 291 980 | 2/1996 |
| GB | 2 339 922 | 2/2000 |
| IL | 143259 | 11/2006 |
| JP | 57-45833 | 3/1982 |
| JP | 63-262613 | 10/1988 |
| JP | 01-111399 | 4/1989 |
| JP | 2002-000556 | 1/1990 |
| JP | 3-289779 | 12/1991 |
| JP | 3289779 | 12/1991 |
| JP | 4109927 | 4/1992 |
| JP | 1992-144533 | 5/1992 |
| JP | 4144533 | 5/1992 |
| JP | 4-180736 | 6/1992 |
| JP | 4180736 | 6/1992 |
| JP | 04-319337 | 11/1992 |
| JP | 6114037 | 4/1994 |
| JP | 6114064 | 4/1994 |
| JP | 06-138400 | 5/1994 |
| JP | 6154191 | 6/1994 |
| JP | 6285044 | 10/1994 |
| JP | 7111985 | 5/1995 |
| JP | 7289504 | 11/1995 |
| JP | 9238900 | 9/1997 |
| JP | 2000-342522 | 12/2000 |
| JP | 2000-342524 | 12/2000 |
| JP | 2000-342525 | 12/2000 |
| JP | 2001-094252 | 4/2001 |
| JP | 2001-112709 | 4/2001 |
| JP | 2001-112710 | 4/2001 |
| JP | 2001-112740 | 4/2001 |
| JP | 2001091860 * | 4/2001 |
| JP | 2001-137182 | 5/2001 |
| JP | 2001137182 | 5/2001 |
| JP | 2001-224551 | 8/2001 |
| JP | 2001-231744 | 8/2001 |
| JP | 2001224553 | 8/2001 |
| JP | 2001-245844 | 9/2001 |
| JP | 2002-010990 | 1/2002 |
| JP | 2003-504815 | 2/2003 |
| JP | 2006-160087 | 6/2006 |
| JP | 2006141897 | 6/2006 |
| WO | WO 92-21307 | 12/1992 |
| WO | WO 92/21307 | 12/1992 |
| WO | WO 98/11816 | 3/1998 |
| WO | WO 99/32028 | 7/1999 |
| WO | WO 00/10456 | 3/2000 |
| WO | WO 00-22975 | 4/2000 |
| WO | WO 00/22975 | 4/2000 |
| WO | WO 00/69324 | 11/2000 |
| WO | WO 01/06917 | 2/2001 |
| WO | WO 01/08548 | 2/2001 |
| WO | WO 01/50941 | 7/2001 |
| WO | WO 01/65995 | 9/2001 |
| WO | WO 01/69212 | 9/2001 |
| WO | WO 02/054932 | 7/2002 |
| WO | WO 02/055126 | 7/2002 |

| | | |
|---|---|---|
| WO | WO 02/055984 | 7/2002 |
| WO | WO 02/067593 | 8/2002 |
| WO | WO 02-067593 | 8/2002 |
| WO | WO 02/080376 | 10/2002 |
| WO | WO 02/094337 | 11/2002 |
| WO | WO 02/094337 | 11/2002 |
| WO | WO 02-095351 | 11/2002 |
| WO | WO 02/095351 | 11/2002 |
| WO | WO 02/102224 | 12/2002 |
| WO | WO 03/003706 | 1/2003 |
| WO | WO 03-003706 | 1/2003 |
| WO | WO 03/011103 | 2/2003 |
| WO | WO 03-011103 | 2/2003 |
| WO | WO 03/094723 | 11/2003 |
| WO | WO 2004/004540 | 1/2004 |
| WO | WO 2004/028335 | 4/2004 |
| WO | WO 2004-028335 | 4/2004 |
| WO | WO 2004/028336 | 4/2004 |
| WO | WO 2004/035105 | 4/2004 |
| WO | WO 2004/035106 | 4/2004 |
| WO | WO 2004/036803 | 4/2004 |
| WO | WO 2004/045395 | 6/2004 |
| WO | WO 2004/059568 | 7/2004 |
| WO | WO 2004/088448 | 10/2004 |
| WO | WO 2006-070360 | 7/2006 |
| WO | WO 2010/010291 | 1/2010 |

OTHER PUBLICATIONS

"Wellesley company sends body montiors into space"—Crum, Apr. 1998.

"Wireless transmission of a color television moving image from the stomach using a miniature CCD camera, light source and microwave transmitter". Swain CP, Gong F, Mills TN. Gastrointest Endosc 1997;45:AB40.

BBC News Online—"Pill camera to 'broadcast from the gut'", Feb. 21, 2000, www.news.bbc.co.uk.

U.S. Appl. No. 11/268,463, filed Nov. 8, 2005, Muratayev et al.

U.S. Appl. No. 10/493,751, filed Apr. 27, 2004, Glukhovsky et al.

Shin-Ichi, et al.: "Robots for the Future", Nov. 29, 2001.

"Video Camera to Take", RF System Lab. Dec. 25, 2001.

Wang, et al.: "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

www.rfnorkia.com-NORIKA3, Dec. 24, 2001.

Office Communication U.S. Appl. No. 10/879,054, mailed Nov. 17, 2005.

International Search Report dated May 19, 2006 from Application No. PCT/IL2005/001380.

Gavriel D. Meron: "The Development of the Swallowable Video Capsule (M2A)" Gastrointestinal Endoscopy, vol. 52, No. 8, Dec. 2000, pp. 817-819.

Appleyard et al. "A Randomized Trial Comparing Wireless Capsule Endoscopy With Push Enteroscopy for the Detection of Small-Bowel Lesions" Gastroenterology, vol. 119, No. 6, Dec. 2000, pp. 1431-1438.

European Search Report Completed Feb. 16, 2005 Application No. 02 738602.8.

European Office Action Dated Dec. 12, 2006 Application No. 02 738602.8.

U.S. Appl. No. 10/166,025, filed Jun. 11, 2002, Lewkowicz et al.

U.S. Appl. No. 10/213,345, filed Aug. 7, 2002, Glukhovsky et al.

Lange et al., Heidelberger Kapsel-ein Kleinstsender fur die Ph-Messung im Magen, Telefunken-Zeitung, Jg 36 (1963) Heft 5, pp. 265-270.

New Smart Plastic has Good Memory-Turke.

Craford et al., In Pursuit of the Ultimate Lamp, Scientific American, Feb. 2001.

Manual of Photogrammetry, Thompson (Ed.), Third Edition, vol. Two, American Society of Photogrammetry.

www.jason.net—Tiny cam © 2000.

www.middleeasthealthmag.com—Review proves the value of computers.

www.pedinc.com—Personal electronic devices © 1997.

The Heidelburg Ph Capsule System Telemetric Fasting Gastric Analysis.

Office Action of U.S. Appl. No. 10/879,054, mailed on Oct. 22, 2009.

Office Action from U.S. Appl. No. 11/280,468, mailed Dec. 16, 2009.

Office Action of U.S. Appl. No. 10/879,258, mailed on Jan. 3, 2007.

Office Action of U.S. Appl. No. 10/879,258, mailed on May 21, 2007.

Office Action of U.S. Appl. No. 10/879,258, mailed on Aug. 12, 2008.

Office Action of U.S. Appl. No. 10/879,258, mailed on Apr. 15, 2009.

Office Action of U.S. Appl. No. 10/879,258, mailed on Aug. 10, 2009.

Final Office Action, issued Feb. 22, 2010, for U.S. Appl. No. 10/879,258.

Office Action, issued Jun. 21, 2010, for U.S. Appl. No. 11/363,185.

Office Action of U.S. Appl. No. 10/879,054 mailed on May 18, 2007.

Office Action of U.S. Appl. No. 10/879,054 mailed on May 16, 2006.

Office Action of U.S. Appl. No. 10/879,054 mailed on Aug. 14, 2008.

Office Action of U.S. Appl. No. 10/879,054 mailed on Mar. 17, 2009.

Office Action of U.S. Appl. No. 10/879,054 mailed on Jan. 22, 2008.

Office Action of U.S. Appl. No. 10/879,054 mailed on Oct. 4, 2006.

Office Action of U.S. Appl. No. 10/879,054 mailed on Nov. 17, 2005.

U.S. Appl. No. 60/298,387, filed Jun. 18, 2001, Avni.

U.S. Appl. No. 10/879,054, filed Jun. 30, 2004, Gilad.

U.S. Appl. No. 60/532,925, filed Dec. 30, 2003, Avron.

U.S. Appl. No. 10/200,548, filed Jul. 23, 2002, Glukhovsky.

U.S. Appl. No. 10/724,109, filed Dec. 1, 2003, Glukhovsky.

U.S. Appl. No. 10/493,751, filed Apr. 27, 2004, Glukhovsky.

U.S. Appl. No. 09/807,892, filed Jun. 6, 2001, Meron.

Gonzalez-Correa et al., "Virtual Biopsies in Barrett's Esophagus Using an Impedance Probe", Annals New York Academy of Sciences, vol. 873, Apr. 1999, pp. 313-321.

United States Office Action of U.S. Appl. No. 11/268,463 dated Mar. 19, 2009.

United States Office Action of U.S. Appl. No. 10/974,979 dated Dec. 19, 2007.

United States Final Office Action of U.S. Appl. No. 10/974,979 dated Jul. 21, 2008.

United States Office Action of U.S. Appl. No. 10/974,979 dated Dec. 26, 2008.

United States Office Action of U.S. Appl. No. 10/974,979 dated Jan. 3, 2007.

United States Final Office Action of U.S. Appl. No. 10/974,979 dated Jul. 17, 2007.

Wang et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html. www.rfnorika.com—NORIKA3 Dec. 24, 2001.

Video Camera to "Take"—RF System Lab, Dec. 25, 2001.

Robots of the future—shin-ichi et al. http://jin.jcic.or.jp/nipponaia13/spos.html.

United States Office Action of U.S. Appl. No. 10/046,541 dated Oct. 20, 2004.

United States Final Office Action of U.S. Appl. No. 10/046,541 dated May 19, 2005.

United States Office Action of U.S. Appl. No. 10/046,541 dated Jan. 12, 2006.

United States Final Office Action of U.S. Appl. No. 10/046,541 dated Jun. 15, 2007.

United States Final Office Action of U.S. Appl. No. 10/046,541 dated Aug. 8, 2007.

United States Office Action of U.S. Appl. No. 10/046,541 dated May 19, 2008.

United States Final Office Action of U.S. Appl. No. 11/094,253 dated Jan. 12, 2010.

United States Final Office Action of U.S. Appl. No. 10/046,541 dated Feb. 17, 2009.

U.S. Appl. No. 11/268,463, filed Nov. 8, 2005, Muratayev.

Gastrointestinal Endoscopy, vol. 45, Apr. 1997, Swain-Gong-Mills.

Dzarnoski et al., "3D Chip Packaging for Class I Medical Devices," Oct. 16, 2008, pp. 50-59 www.wlcspforum.org/member_area/proceedings/IWLPC_2008/PDSs/Papers/08.pdf.

Fjelstad et al., "Flexible Circuit Technology, 3rd Edition", Sep. 2006, pp. 1-233 www.scribd.com/doc/37078218/Flexible-Circuit-Technology-3rd-A.

U.S. Appl. No. 10/974,979, filed Oct. 28, 2004, Avron, Jerome.
U.S. Appl. No. 60/297,761, Lewkowicz et al.
U.S. Appl. No. 60/301,141, Glukhovsky et al.
U.S. Appl. No. 60/309,181, Glukhovsky.
Office Action, issued Sep. 23, 2010, for U.S. Appl. No. 11/603,123.
Notice of Allowance, issued Mar. 23, 2010, for U.S. Appl. No. 11/094,253.
Katzgraber F, Glenewinkel F, Fischler S, Rittner C. "Mechanism of fatal air embolism after gastrointestinal endoscopy," Int. J. Legal Med, 1998; 111(3):154-156.
"Bio-Medical Telemetry: Sensing and Transmitting Biological Information from Animals and Man," R. Stuart Mackay, John Wiley and Sons, New York, 1970, pp. 244-245.
"Deep Subsurface Imaging in Tissues Using Spectral and Polarization Filtering," S.G. Demos, Jul. 3, 2000, vol. 7, No. 1, Optics Express, pp. 23-28.
"Evaluation of the Heidelberg pH Capsule: Method of Tubeless Gastric Analysis," Yarbrough III et al., The American Journal of Surgery, vol. 117, Feb. 1969, pp. 185-192.
Final Office Action, issued Mar. 8, 2011, for U.S. Appl. No. 11/603,123.
Notice of Allowance, issued Jul. 14, 2010, for U.S. Appl. No. 11/094,253.
Office Action for U.S. Appl. No. 11/280,468, dated Jun. 16, 2009.
Office Action for U.S. Appl. No. 11/094,253, dated Jul. 6, 2009.

* cited by examiner

IN VIVO SENSING DEVICE WITH A CIRCUIT BOARD HAVING RIGID SECTIONS AND FLEXIBLE SECTIONS

CROSS-REFERENCE TO RELATED APPLICATIONS

This application is a National Phase Application of PCT International Application No. PCT/IL02/00480, International Filing Date Jun. 18, 2002, entitled "IN VIVO SENSING DEVICE WITH A CIRCUIT BOARD HAVING RIGID SECTIONS AND FLEXIBLE SECTIONS", which in turn claims priority from U.S. Provisional Patent Application 60/298,387, filed Jun. 18, 2001, which are both incorporated by reference herein in their entirety.

FIELD OF THE INVENTION

The present invention relates to an in vivo imaging device and system such as for imaging the digestive tract.

BACKGROUND OF THE INVENTION

In vivo imaging may include the use of an in vivo imager from which image data may be transmitted to an external receiving system. For example, an ingestible capsule comprising an image sensor and a transmitter for transmitting image data may be used for imaging the gastrointestinal (GI) tract. In some ingestible capsules the electronic components within the capsule may be arranged on several boards, each board containing different components of the capsule, for example, the image sensor, typically a silicon chip, may be positioned on one board whereas the transmitter may be positioned on a separate printed circuit board (PCB). In some cases the boards are aligned along an axis of the capsule and are electrically connected by a plurality of wires. Assembly of capsules having several boards connected by wires may be complex and may hinder, for example, large scale production.

SUMMARY OF THE INVENTION

Thus, the present invention provides, according to some embodiments an in vivo sensing device comprising a circuit board having a plurality of rigid sections and a plurality of flexible sections. According to one embodiment the rigid sections and flexible sections alternate. Optionally, the in vivo sensing device may include at least an image sensor. According to another embodiment the device may also include a transmitter for transmitting signals from a sensors such as an imaging camera, to a receiving system. In one embodiment various components in the device, such as the image sensor and transmitter, are disposed on different rigid circuit board sections. Preferably, the circuit board is folded and arranged in a stacked vertical fashion In a further embodiment, the various rigid portions may be connected by vertical connectors such as springs.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention However, it will also be apparent to one skilled in the art that the present invention may be practiced without the specific details presented herein. Furthermore, well-known features may be omitted or simplified in order not to obscure the present invention.

The system and method of the present invention may be used with an imaging system such as that described in WO 01/65995. A further example of an imaging system with which the system and method of the present invention may be used is described in U.S. Pat. No. 5,604,531 to Iddan et al. Both these publications are assigned to the common assignee of the present application and are hereby incorporated by reference. Alternatively, the system of the present invention may be utilized in any suitable imaging device providing images of a body lumen or cavity. For example, a circuit board according to an embodiment of the invention may be utilized in probes used for in vivo imaging, such as endoscopes.

Figure 1:
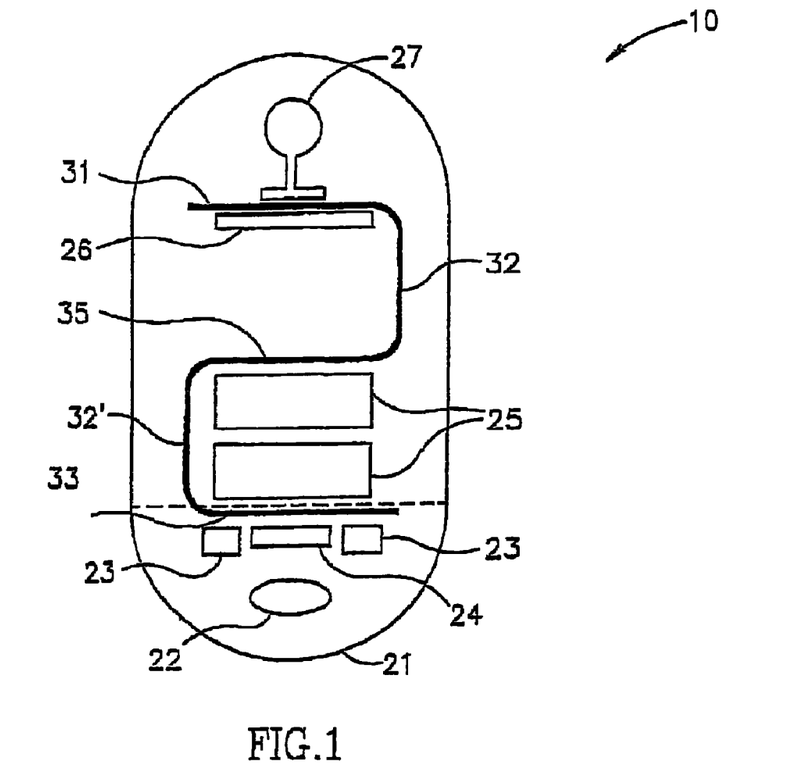
FIG. 1 schematically illustrates an in vivo imaging device according to one embodiment of the invention.

Reference is now made to FIG. 1, which schematically illustrates an in vivo imaging device according to an embodiment of the invention. The device 10 typically comprises an optical window 21 and an imaging system for obtaining images from inside a body lumen, such as the GI tract. The imaging system includes an illumination source 23, such as a white LED, a CMOS imaging camera 24, which detects the images and an optical system 22 which focuses the images onto the CMOS image sensor 24. The illumination source 23 illuminates the inner portions of the body lumen through optical window 21. Device 10 further includes a transmitter 26 and an antenna 27 for transmitting image signals from the CMOS image sensor 24, and a power source 25, such as a silver oxide battery, that provides power to the electrical elements of the device 10. A suitable CMOS image sensor 24 is, for example, a "camera on a chip" type CMOS imager specified by Given Imaging Ltd. of Yokneam, Israel and designed by Photobit Corporation of California, [[USA,]] USA. The single chip camera can provide either black and white or color signals. A suitable transmitter may comprise a modulator which receives the image signal (either digital or analog) from the CMOS imaging camera, a radio frequency (RF) amplifier, an impedance matcher and an antenna. A processor, e.g., for processing the image data may be included in the device. The processor or processing circuitry may be integrated in the sensor or in the transmitter.

The device 10 is capsule shaped and can operate as an autonomous endoscope for imaging the GI tract. However, other devices, such as devices designed to be incorporated in an endoscope, catheter, stent, needle, etc., may also be used, according to embodiments of the invention. Furthermore, the device 10 need not include all the elements described above. For example, the device 10 need not include an internal light source or an internal power source; illumination and/or power may be provided from an external source, as known in the art.

According to one embodiment of the invention, the various components of the device 10 are disposed on a circuit board including rigid and flexible portions; preferably the components are arranged in a stacked vertical fashion. For example, one rigid portion 31 of the circuit board may hold a transmitter and an antenna; preferably the antenna is at one end of the capsule to avoid screening of the signal by metal or other components in the capsule. Another rigid portion 33 of the circuit board includes an LED 23 lighting system and an imager 24 on one side; the other side of this rigid portion 33 includes a battery 25 contact. The battery contact is preferably a spring, described below. Another rigid portion 35 of the circuit board includes another battery contact. Each rigid portion of the circuit board is connected to another rigid portion of the circuit board by a flexible connector portion (e.g. 32 and 32') of the circuit board. Preferably, each rigid portion of the circuit board comprises two rigid sections; sandwiched between the rigid sections is a flexible connector portion of the circuit board for connecting the rigid boards. In alternate embodiments, other arrangements of components may be placed on a circuit board having rigid portions connected by flexible portions.

In alternate embodiments, a circuit board having rigid portions and flexible portions may be used to arrange and hold components in other in vivo sensing devices, such as a swallowable capsule measuring acidity (having a pH sensor), temperature or pressure, or in a swallowable imaging capsule having components other than those described above.

Preferably, each flexible connector portion is equal to or less than $4/1000$ inch (4 mils) in thickness. Preferably, electrical connection is made from the outside portion of a rigid portions of a board (on which components are mounted) to the inside of the rigid portion and to the flexible portion contained within, by a small (equal to or less than 4 mils in diameter) hole leading from the outside portion to the flexible portion—a micro-via. Preferably the micro-via is created using a laser. Companies providing such flexible connector and micro-via technology are Eltech, of Petach-Tikva, Israel, and Ilfa, of Germany. In alternate embodiments, other types of rigid sections and flexible sections may be used to create a circuit board.

Figure 2A:
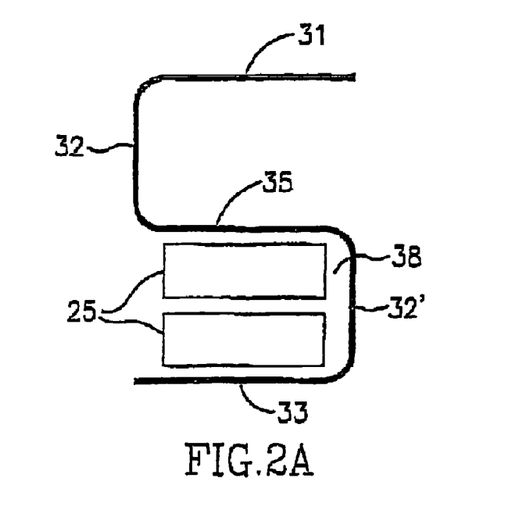
FIGS. 2A and 2B schematically illustrate possible folding of the circuit board according to two embodiments of the invention.
Figure 2B:
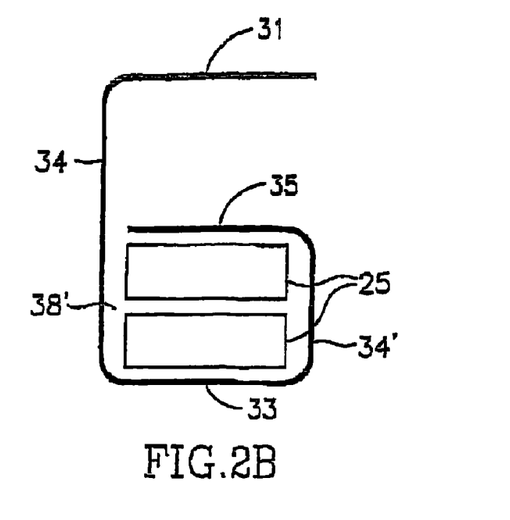

The circuit board may be folded, for example, as shown in FIGS. 2A and 2B. When folded, the battery contacts contact a set of one or more batteries, which are sandwiched between two rigid circuit board portions. The circuit board may be folded in various manners. For example, FIG. 2A schematically shows a circuit board, according to an embodiment of the invention, arranged as an "S" with rigid portions 31, 35 and 33 and alternating flexible portions 32 and 32'. A set of batteries 25 may be sandwiched between one lobe 38 of the S. Another configuration, according to an embodiment of the invention is schematically shown in FIG. 2B. The circuit board, according to an embodiment of the invention may be in the shape of a "6" with rigid portions 31, 35 and 33 and alternating flexible portions 34 and 34'. A set of batteries 25 may be positioned in the closed configuration 38' of the "6". Other configurations are possible. In alternate embodiments, batteries may be connected in different manners, or need not be used.

Preferably, a very thin flexible section is needed due to the radius of the diameter of the turns, given the size of the capsule, and also because the flexible section may be disposed between components, such as between the set of batteries and the side of the capsule. Preferably, the radius of the turn should be more than 6 or 10 times the thickness. In alternate embodiments, the rigid boards and flexible connectors may be of other dimensions.

In one embodiment, the rigid portions of the circuit board may include any sort of known material; preferably FR4 flexiglass is used. The flexible portions may include any sort of known material; preferably, Kaptonm™ by DuPont is used.

Figure 3:
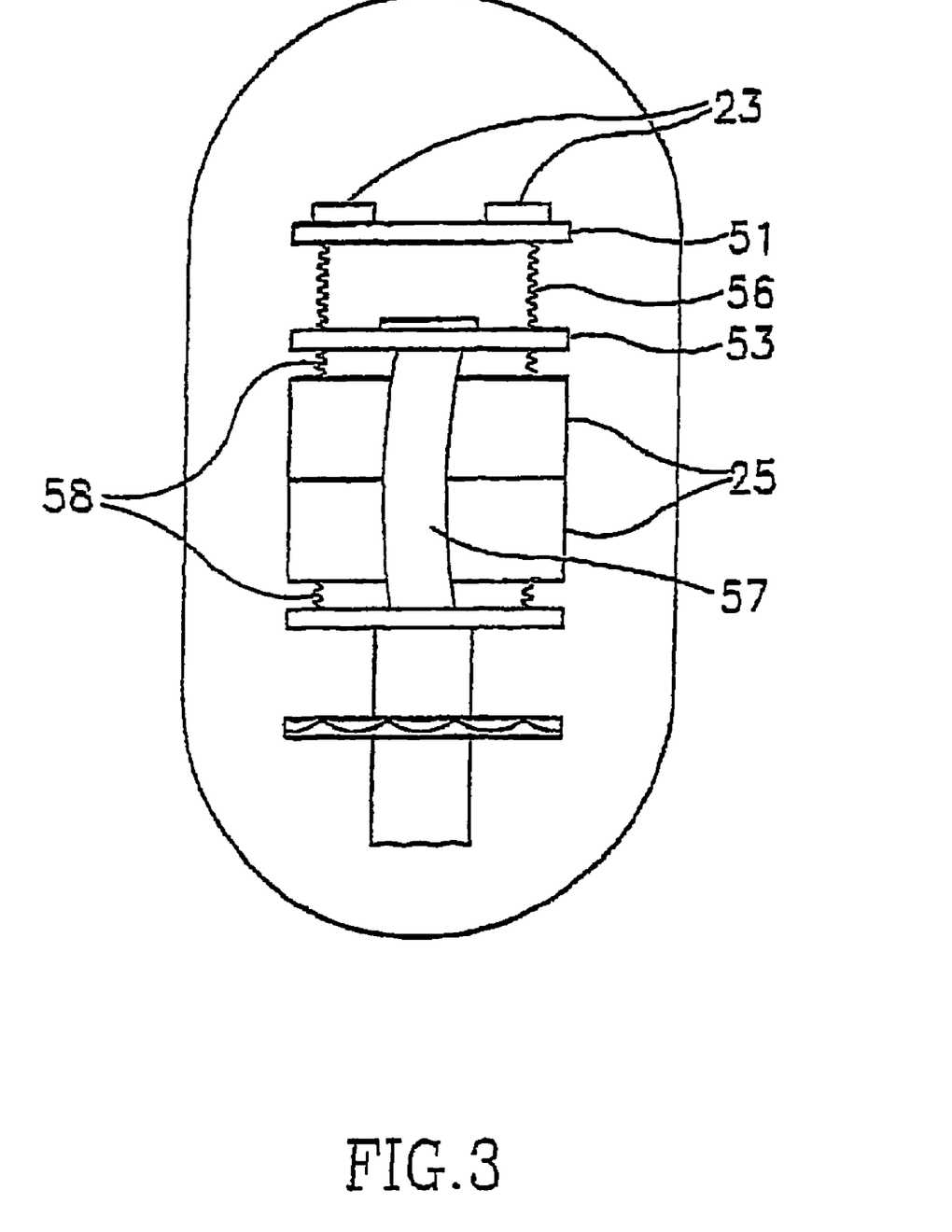
FIG. 3 schematically illustrates an in vivo imaging device according to a third embodiment of the invention.
Figure 4:
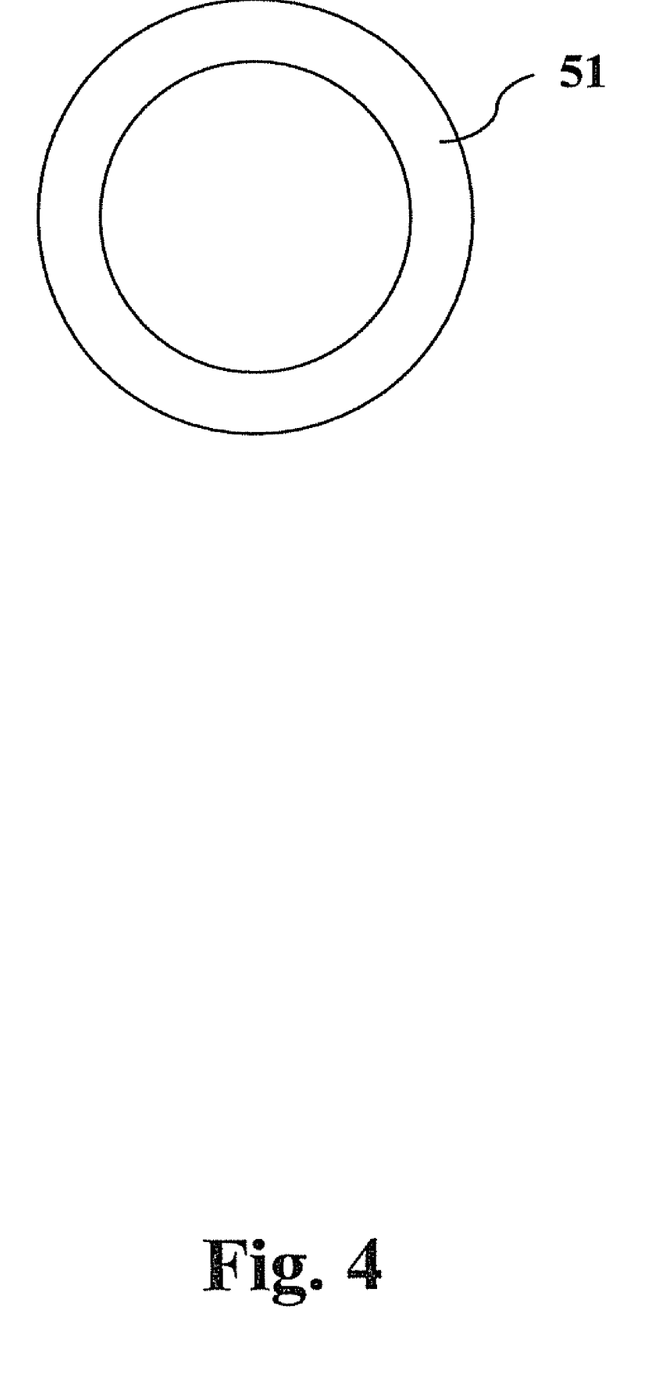
FIG. 4 schematically illustrates a circuit board according to one embodiment of the invention.

Reference is made to FIG. 3, which schematically illustrates another view of an embodiment of the invention. According to one embodiment, a vertical physical and electrical connection may be made between rigid portions of the circuit board. For example, the rigid portion 51 holding the LED 23 (which is preferably in the shape of a ring, as for example shown in FIG. 4) may be connected physically and electrically to another rigid portion apart from being connected by flexible portion 57. In one embodiment, mini springs 56 are used to connect a power supply from one circuit rigid portion 53 to the rigid portion 51 holding the LED 23. Such springs 56 have two functions; to mechanically connect the two rigid portions (e.g., 51 and 53) and also to conduct current between the two rigid portions. Preferably, the springs are glued to the two rigid portions, and current flows between two rigid portions.

In addition, a vertical connection is made between the set of batteries 25 and two rigid portions by springs 58. Each contact spring 58 is preferably a conical spring, which, as it shrinks, allows each circle or coil of the spring to enter a larger encircling coil. Thus, when fully shrunken, the final thickness of the spring is thickness of a single circle of conductor wire.

There is also provided a method for the manufacture of an in vivo sensor, in accordance with an embodiment of the invention. The method includes the steps of disposing at least a sensor on a rigid section of a circuit board having a plurality of rigid sections and a plurality of flexible sections and folding the circuit board into a housing configured for in vivo sensing.

It will be appreciated by persons skilled in the art that the present invention is not limited to what has been particularly shown and described hereinabove. Rather the scope of the present invention is defined only by the claims which follow:

The invention claimed is:

1. A swallowable in vivo sensing device comprising:
   a circuit board that comprises a plurality of rigid sections, at least two of the rigid sections being connected by a flexible section, and one or more batteries being positioned between the two rigid sections, the swallowable in vivo sensing capsule further comprising an illumination source electrically connected to at least one rigid section of the circuit board, wherein the rigid section to which the illumination source is electrically connected is ring shaped.

2. The device according to claim 1 wherein the circuit board is folded within the device such that the rigid sections of the circuit board are stacked in a column along the axis of the device such that the rigid sections are parallel to one another.

3. The device according to claim 1 and also comprising a sensor.

4. The device according to claim 3 wherein the sensor is an image sensor.

5. The device according to claim 3 wherein the sensor is selected from the group consisting of a pH sensor, a temperature sensor and a pressure sensor.

6. The device according to claim 3 and also comprising a transmitter.

7. The device according to claim 6 wherein the sensor is disposed on a rigid section of the circuit board and the transmitter is disposed on another rigid section of the circuit board.

8. The device according to claim 1 further comprising at least one component selected from the group consisting of, a sensor, a processor, a transmitter or a combination thereof.

9. The device according to claim 8 wherein at least one component is disposed on at least one rigid section of the circuit board.

10. The device according to claim 8 wherein a plurality of components are disposed on a plurality of rigid sections of the circuit board.

11. The device according to claim 1 wherein the rigid sections alternate with flexible sections.

12. The device according to claim 1 wherein the circuit board is folded such that the rigid sections of the circuit board are stacked vertically.

13. The device according to claim 1 wherein the rigid sections are connected by vertical connectors.

14. The device according to claim 13 wherein the vertical connectors are electrical conductors.

15. The device according to claim 13 wherein the vertical connectors are springs.

16. The device according to claim 15 wherein the springs are conical springs.

17. The device according to claim 1 wherein the circuit board includes flexiglass.

18. A swallowable in vivo sensing device comprising:
   a circuit board comprising a plurality of rigid sections forming rigid portions and a flexible connector portion, wherein the flexible connector portion connects the rigid portions;
   an illumination source electrically connected to at least one rigid section of the circuit board, wherein the rigid section to which the illumination source is electrically connected is ring shaped;
   a transmitter; and
   a battery being positioned between two of the rigid portions.

19. The device according to claim 18 comprising an image sensor.

20. The device according to claim 18 comprising an image sensor disposed on a rigid portion.

21. The device according to claim 18 wherein the transmitter is disposed on a rigid portion.

22. A method for the manufacture of an in vivo sensor, the method comprising the steps of:
   disposing at least a sensor on a rigid section of a circuit board having a battery contact and a plurality of rigid sections wherein at least two of the rigid sections are connected by a flexible section; and
   folding the circuit board into a housing configured for in vivo sensing such that at least one battery is positioned between the two rigid sections, the battery contact included on a rigid section,
   wherein an illumination source is electrically connected to at least one rigid section of the circuit board, and wherein the rigid section to which the illumination source is electrically connected is ring shaped.

23. The method according to claim 22 wherein the step of folding the circuit board includes folding the circuit board such that the rigid sections of the circuit board are stacked vertically.

24. The method according to claim 22 wherein an antenna is positioned on at least one rigid section, the antenna protruding from the at least one rigid section into a space at one end of the housing.

* * * * *